United States Patent [19]

Schmidbaur et al.

[11] 4,185,028

[45] Jan. 22, 1980

[54] DOUBLE YLIDE COMPLEXES OF METALS AND PROCESS FOR MAKING THEM

[75] Inventors: Hubert Schmidbaur, Garching; Hans-Jürgen Fuller, Unterpfaffenhofen, both of Fed. Rep. of Germany

[73] Assignee: Hoechst Aktiengesellschaft, Fed. Rep. of Germany

[21] Appl. No.: 868,830

[22] Filed: Jan. 12, 1978

[30] Foreign Application Priority Data

Jan. 13, 1977 [DE] Fed. Rep. of Germany ....... 2701143

[51] Int. Cl.² .............................................. C07F 1/12
[52] U.S. Cl. ................. 260/430; 260/429 R; 260/429.9; 260/439 R; 260/448 A; 260/606.5 P
[58] Field of Search ................ 260/429 R, 429.9, 430, 260/439 R, 606.5 P, 448 A

[56] References Cited

U.S. PATENT DOCUMENTS

| | | | |
|---|---|---|---|
| 2,998,416 | 8/1961 | Mendel | 260/606.5 P X |
| 3,414,624 | 12/1968 | Peterson et al. | 260/606.5 P |
| 4,083,875 | 4/1978 | Schmidbaur et al. | 260/429 R X |
| 4,097,509 | 6/1978 | Schmidbaur et al. | 260/429 R |

OTHER PUBLICATIONS

Chemical Abstracts, 85 160249w (1976).

*Primary Examiner*—Helen M. S. Sneed
*Attorney, Agent, or Firm*—Connolly and Hutz

[57] ABSTRACT

Double ylide complexes of metals are made by reacting trimethylphosphin-imino-dimethyl-methylene phosphorane of the formula

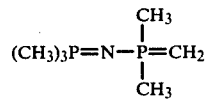

with one or more compounds of the metals nickel, palladium, platinum, gold, zinc, cadmium, aluminum, gallium, indium, thallium, magnesium or lithium.

The novel double ylide complexes comprise various metal-bis[nitrido-bis(dimethylphosphonium methylides)], dimethyl-metal[nitrido-bis(dimethylphosphonium methylides)], and lithium-[nitrido-bis(dimethylphosphonium methylide)].

8 Claims, No Drawings

DOUBLE YLIDE COMPLEXES OF METALS AND PROCESS FOR MAKING THEM

This invention relates to double ylide complexes of metal, and to their preparation and their use as catalysts or co-catalysts in the polymerisation of olefins.

The preparation of trimethylphosphinimino-dimethylmethylene phosphorane of the formula

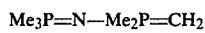

Me$_3$P=N—Me$_2$P=CH$_2$ (where Me=CH$_3$)
has already been described (H. Schmidbaur and H. J. Fuller, Angew. Chem. 88 (1976), page 541). As how now been found, this compound, referred to below simply as TDMP, can be reacted with compounds of various metals to give novel and technically interesting double ylide complexes of metals.

The invention relates more particularly to a process for making double ylide complexes of metals, which comprises reacting TDMP with one or more compounds of the following metals: Ni, Pd, Pt, Au, Zn, Cd, Al, Ga, In, Tl, Mg, Li.

Preferred features of the present process provide:
(a) for the above-mentioned one or more compounds of metals to comprise one or more compounds of the following formulae: (Me$_3$P)$_2$MX$_2$; MX$_2$; (Me$_3$P)$_2$NiMeX; (Me$_3$P)$_2$NiMe$_3$; (Me$_2$AuX)$_2$; LiR; M'R$_2$; M"R$_3$; in which Me=CH$_3$, M is Ni, Pd or Pt, X is Cl, Br or I, M' is Mg, Zn or Cd, M" is Al, Ga, In or Tl, and R is Me, C$_2$H$_5$, C$_3$H$_7$ or C$_4$H$_9$;
(b) for a metal-bis[nitrido-bis(dimethylphosphonium methylide)] of the formula

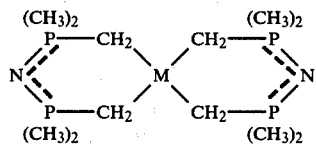

in which M is Ni, Pd or Pt, to be made by reacting TDMP with (Me$_3$P)$_2$MCl$_2$ in which M is Ni, Pd or Pt in an inert organic solvent at temperatures of 10° to 110° C.;

(c) for a metal-bis[nitrido-bis(dimethylphosphonium methylide)], of the formula

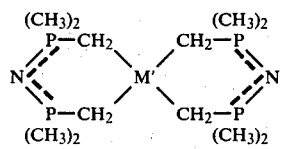

in which M' is Mg, Zn or Cd, to be made by reacting TDMP with agitation with MgR$_2$, ZnR$_2$ or CdR$_2$, in which R is Me or C$_2$H$_5$, in an inert organic solvent at temperatures of 10° to 110° C. until evolution of gas has died down;

(d) for dimethyl gold-[nitrido-bis(dimethyl-phosphonium methylide)] of the formula:

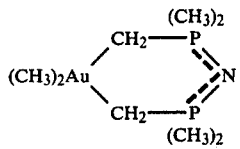

to be made by reacting TDMP with (Me$_2$AuCl)$_2$, i.e., bis[dimethyl gold(III) chloride], in an inert organic solvent at temperatures of 10° to 110° C.;

(e) for a dimethyl-metal[nitrido-bis(dimethylphosphonium-methylide)], of the formula

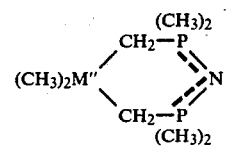

in which M" is Al, Ga, In or Tl, to be made by reacting TDMP with agitation with M"R$_3$, in which R is Me or C$_2$H$_5$, in an inert organic solvent at temperatures of 0° to 110° C. until evolution of gas has died down;

(f) for lithium-[nitrido-bis(dimethylphosphonium methylide)] of the formula

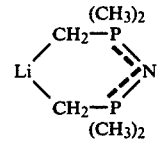

to be made by reacting TDMP with n-butyl lithium in an inert organic solvent at temperatures of 0° to 110° C. until evolution of gas has died down; and (g) for the inert solvent employed in case "(b)," "(c)," "(d)," "(e)" or "(f)" to comprise diethylether, benzene, toluene, ortho- meta- or para-xylene, dioxan or cyclohexane.

The invention also includes the following compounds per se:
a metal bis[nitrido-bis(dimethylphosphonium methylide)] of the formula

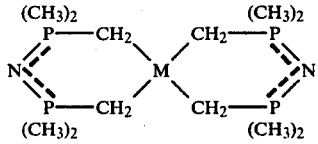

in which M is Ni, Pd, Pt, Mg, Zn or Cd; a dimethyl-metal-[nitrido-bis(dimethylphosphonium methylide)] of the formula

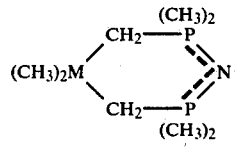

in which M is Au, Al, Ga, In or Tl; and lithium[nitrido-bis(dimethylphosphonium methylide)] of the formula

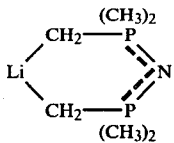

The invention additionally includes the use of compounds falling per se within its scope, or prepared by the process of the invention, as catalysts or co-catalysts in the polymerization of olefins (cf. U.S. Pat. Nos. 2,998,416 and 3,686,159). The preparation of the double ylide complexes of Ni, Pd, Pt and Au takes the course of a re-ylidation reaction, as shown by the following equations "1" and "2," in which bis-trimethyl-phosphoranylidene ammonium chloride is separated, trimethylphosphine being liberated in "1" though not in "2."

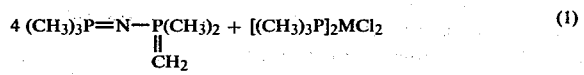

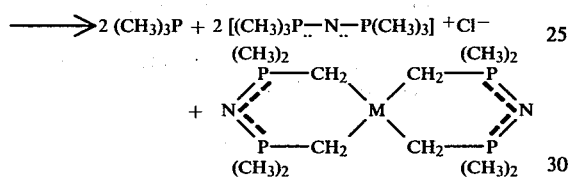

In equation "1," M is Ni, Pt or Pd; the M-containing products are referred to below simply as compounds "(I)," "(II)" and "(IIa)" respectively.

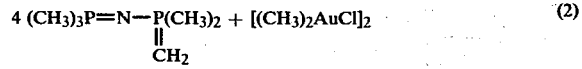

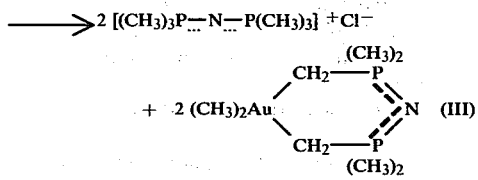

The compounds "(I)," "(II)" and "(III)" comprise yellow or colourless crystals which are readily soluble in organic solvents. They are obtained in yields of the order of 90% of the theoretical.

In the mass spectra, the respective molecule ions appear with high intensity. Greater masses are not observed, so that further aggregation of the complexes is to be considered unlikely.

The $^1$H- and $^{31}$P-NMR-spectra observed when solutions of compounds "(I)" and "(II)" are examined indicate consistently the exclusive presence of highly symmetrical molecules in which the four $(CH_3)_2PCH_2$-groups are structurally equivalent. In compound "(III)," the two Me groups on the Au atom are equivalent, and also the two $(CH_3)_2PCH_2$-groups are equivalent. In the $^1$H-spectra, the platinum compound "(II)" shows a reciprocal or alternating effect in respect of the above-indicated nuclei and $^{195}$Pt, which is clear evidence of the strong covalent linkage of the ligand to the central atom. In other words, the complexes concerned can be regarded as true organometallic compounds.

Complete X-ray structural analysis has given clear evidence confirming the above-indicated structure of compound "(I)."

Subjecting a magnesium-, zinc- or cadmium dialkyl to reaction with TDMP directly yields a 1:2 complex together with an alkane, in accordance with the the following equation "3":

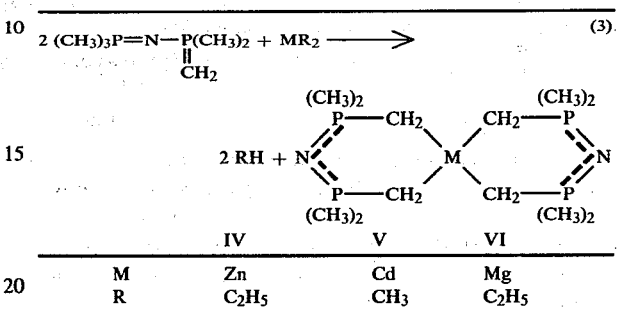

| | IV | V | VI |
|---|---|---|---|
| M | Zn | Cd | Mg |
| R | $C_2H_5$ | $CH_3$ | $C_2H_5$ |

Trimethylgallim undergoes the reaction shown in equation "4" below with the resultant formation of a 1:1 adduct which can be heated to obtain a double ylide complex of formula "(VII)," methane being split off.

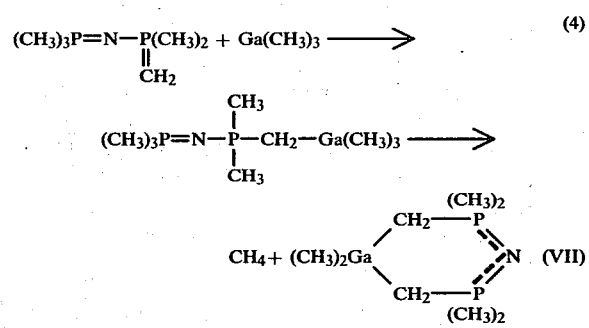

Trimethylthallium can be reacted in an analogous manner to produce a similar double ylide complex of formula "(VIII)," which melts at 116° C. with decomposition. Even if carried out at room temperature, however, the reaction does not in this case give a 1:1 adduct as an initial product; instead, methane is evolved immediately, in accordance with the following equation "5":

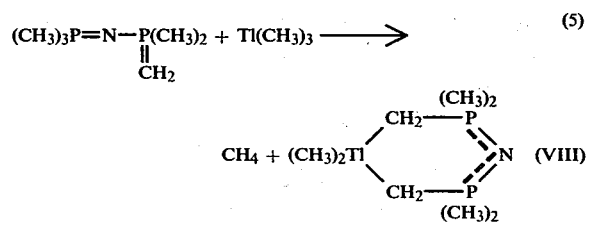

The aluminum and indium compounds react in an analogous manner. Lithiumalkyls, e.g., n-butyllithium, undergo a comparable reaction in accordance with the following equation "6":

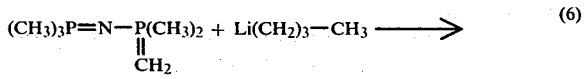

-continued

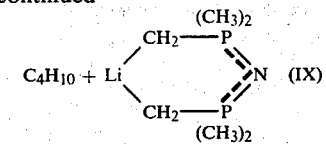

An ethereal solution of compound "(IX)" presumably contains a solvate of the following formula:

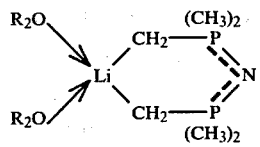

in which R is methyl, ethyl or another alkyl group.

The following Examples illustrate the invention.

EXAMPLE 1

Nickel-bis[nitrido-bis(dimethylphosphonium methylide)] (compound "(I)")

0.76 g of bis-trimethylphosphine nickel dichloride (Me$_3$P)$_2$NiCl$_2$ (2.61 mmol) was suspended in 30 ml of benzene and the suspension was admixed with 1.73 g (10.5 mmol) of TDMP. The whole was stirred for 5 hours and precipitated bis-trimethylphosphoranylidene-ammonium chloride was filtered off and washed with a small quantity of benzene; the filtrate was (including washings) freed under vacuum for the trimethylphosphine which had been liberated, and from the benzene solvent. The remaining yellow residue was capable of being crystallized from a 50:50 mixture of toluene and n-pentane, or alternatively of being sublimed at 105° C. under a pressure of $10^{-4}$ mm Hg. The compound "(I)" was obtained in a yield of 0.95 g, corresponding to 94% of the theoretical, in the form of yellow needles. It melted at 230° C. (with partial decomposition).

Presumptive formula: C$_{12}$H$_{32}$N$_2$NiP$_4$ (formula weight 387.0): Calculated: C, 37.24; H, 8.33; Found: C, 36.80; H, 8.31.

Molar mass: 386 (mass spectrum; $^{58}$Ni).

EXAMPLE 2

Platinum-bis[nitrido-bis(dimethylphosphonium methylide)] (compound "(II)"

1.20 g (2.88 mmol) of bis-trimethylphosphine platinum dichloride (Me$_3$P)$_2$PtCl$_2$ and 1.90 g (11.5 mmol) of TDMP were reacted in the manner described in Example 1; the compound "(II)" was obtained in a yield of 1.45 gram, corresponding to 91% of the theoretical, in the form of white crystals having a sublimation point of 120° under $10^{-4}$ mm Hg; and a melting point of 233° C. (with decomposition).

Presumptive formula: C$_{12}$H$_{32}$N$_2$P$_4$Pt (formula weight 523.38): Calculated: C, 27.53; H, 6.16; Found: C, 27.42; H, 6.14.

Molar mass: 522 (mass spectrum, $^{195}$Pt).

EXAMPLE 3

Dimethylgold[nitrido-bis(dimethylphosphonium methylide)] (compound "(III)")

240 mg (0.46 mmol) of bis[dimethylgold(III)-chloride] (Me$_2$AuCl)$_2$ and 320 mg (1.94 mmol) of TDMP were reacted, in the manner described in Example 1, in 10 of benzene; the compound "(III)" was obtained in a yield of 310 mg corresponding to 87% of the theoretical, in the form of colourless crystalline material. Sublimation point: 100° C./$10^{-1}$ mm Hg; melting point: 155° C.; decomposition point: 268° C. (with formation of a gold mirror).

Presumptive formula: C$_8$H$_{22}$AuNP$_2$ (formula weight 391.1): Calculated: C, 24.56; H, 5.66; Au, 50.35; Found: C, 24.65; H, 5.65; Au, 49.75.

Molar mass: 391 (mass spectrum).

The by-products obtained in Examples 1 to 3 were examined by IR and NMR-spectroscopy. (Me$_3$PN-PMe$_3$)Cl was obtained almost quantitatively in each case.

EXAMPLE 4

Zinc-bis[nitrido-bis(dimethylphosphonium methylide)] (compound "(IV)")

0.615 g (5 mmol) of zinc diethyl was dissolved in 20 ml of benzene, and the resulting solution was admixed with 1.65 g (10 mmol) of TDMP. The clear reaction mixture thus formed was stirred at 20° C. for about 12 hours until the evolution of gas had died down, and was then freed from the benzene solvent under vacuum. The gas evolved was subjected to gas chromatography, and identified as ethane. The crude product was purified by distillation. Boiling point: 110° C. under 0.1 mm Hg; melting point: 75°–77° C. The compound "(IV)" was obtained in a yield of 2.08 g (98% of the theoretical) in the form of colourless soft crystals which were soluble in aprotic organic solvents, and were susceptible to oxidation and hydrolysis.

Presumptive formula: C$_{12}$H$_{32}$N$_2$P$_4$Zn formula weight 393.67): Calculated: C, 36.61; H, 8.19; Found: C, 36.33; H, 8.27.

EXAMPLE 5

Cadmium-bis[nitrido-bis(dimethylphosphonium methylide)] (compound "(V)")

1.0 g of cadmium dimethyl (7.0 mmol) was reacted as described in Example 4 with 2.3 g (13.9 mmol) of TDMP in 20 ml of benzene. The compound "(V)" was obtained in a yield of 3.1 g, corresponding to 88.5% of the theoretical. Methane was obtained as a by-product. Boiling point: 120° C. under 0.1 mm Hg; melting point: 86°–88° C. The product was slightly yellowish, but otherwise had properties similar to those of compound "(IV)."

Presumptive formula: C$_{12}$H$_{32}$CdN$_2$P$_4$(formula weight 440.7): Calculated: C, 32.71; H, 7.32; Found: C, 32.52; H, 7.32.

EXAMPLE 6

Magnesium-bis[nitrido-bis(dimethylphosphonium methylide)] (compound "(VI)")

A solution of 1.4 g (8.50 mmol) of TDMP in 10 ml of benzene was admixed at 20° C. with a dioxan solution with a known content of magnesium diethyl dioxanate (4.25 mmol). The evolution of ethane commenced at a temperature as low as 20° C., and occurred more rapidly under reflux heating, but was terminated after 25 hours. The benzene-dioxan solvent was removed, and the residue was distilled. Boiling point: 128°–130° C. under $10^{-4}$ mm Hg. The compound "(VI)" was obtained in a yield of 1.36 g, corresponding to 90.7% of the theoretical. Melting point: 71° C. The compound was obtained as a highly reactive hygroscopic mass, which could not be weighed for C and H analysis. It was colourless and evolved considerable smoke in contact with air.

Presumptive formula: $C_{12}H_{32}MgN_2P_4$ (formula weight 352.61): Calculated: Mg, 6.89; Found: Mg, 7.01 and 6.92.

Molar mass: $M^+ = 352$ (mass spectrum).

EXAMPLE 7

Dimethylgallium-[nitrido-bis(dimethylphosphonium-methylide)] (compound "(VII)")

2.26 g (12.0 mmol) of trimethylgallium etherate was dissolved in 20 ml of ether, and the resulting solution was cooled to 0° C. A solution of 1.98 g (12.0 mmol) of TDMP in 10 ml of ether, also cooled to 0° C., was added, but no gas evolution could be seen. The whole was heated for 2 hours with agitation to 20° C., the solvent was removed under vacuum, and the residue was crystallized by cooling down to $-78°$ C. from a 50:50 mixture of toluene and pentane. An intermediate product was obtained in a yield of 3.05 g, corresponding to 90.8% of the theoretical; this was the adduct [(trimethylphosphinimino)dimethylphosphonium methylide]-trimethylgallium, in the form of colourless waxy crystals highly sensitive to air. Melting point: 27° C. (with decomposition). $^1$H-NMR (in benzene at 25° C., TMS ext.): $\delta$ $(CH_3)_3P$ 0.98 ppm, d, 9H, J(HCP) 13.1 Hz; $\delta$ $(CH_3)_2P$ 1.34, d, 6H, J(HCP) 13.9; $CH_2$ 0.53; d, 2H, J(HCP) 17.2; $\delta$ $CH_3Ga$—0.03, s, 9H.

Presumptive formula: $C_9H_{26}GaNP_2$ (formula weight 279.98): Calculated: C, 38.61 H, 9.36 Found: C, 37.90 H, 9.12

To obtain the compound "(VII)," 2.5 g (8.93 mmol) of the adduct was heated for 2 hours under reflux in 10 ml of benzene, methane being split off. The solvent was removed under vacuum. The yellowish residue was purified by sublimation at 65° C. under 0.1 mm Hg, and colourless crystals melting at 70° C. were obtained. The compound "(VII)" was obtained in a yield of 2.28 g, corresponding to 96.7% of the theoretical.

Presumptive formula: $C_8H_{22}GaNP_2$ (formula weight 263.94): Calculated: C, 36.40; H, 8.40; N, 5.31; Found: C, 35.8; H, 8.58; N, 4.91.

Molar mass: $M^+$-15 = 248 ($^{69}$Ga, mass spectrum).

EXAMPLE 8

Dimethylthallium-[nitrido-bis(dimethylphosphonium-methylide)] (compound "(VIII)")

1.92 g (7.70 mmol) of trimethylthallium in 30 ml of ether was reacted at 20° C. with 1.27 g (7.70 mmol) of TDMP. A gas began to evolve immediately; it was identified as methane by gas chromatography. The evolution of gas was terminated after 24 hours. The ether solvent was removed, and the product was crystallized from a 50:50 mixture of toluene and pentane. The compound "(VIII)" was obtained in a yield of 2.48 g, corresponding to 81% of the theoretical, in the form of colourless crystals which were only very slightly sensitive to air. Melting point: 116° C. (with decomposition).

Presumptive formula: $C_8H_{22}NP_2Tl$ (formula weight: 398.59) Calculated: C, 24.11; H, 5.56; Found: C, 24.8; H, 5.18.

Molar mass: $M^+$-15 = 384 ($^{205}$Tl, mass spectrum).

EXAMPLE 9

Lithium-[nitrido-bis(dimethylphosphonium-methylide)] (compound "(IX)")

An ethereal solution of TDMP was reacted at room temperature with 1 equivalent of n-butyllithium. This reaction was accompanied by the evolution of 1 equivalent of n-butane. The resulting lithium complex, i.e., compound "(IX)," remained in solution, and was used in this form. It was found inadvisable to isolate it because of its variable solvate content.

TABLE:

| | | \multicolumn{8}{c}{NMR-data of compounds "(I)" to "(VIII)"} | | | | | | | |
|---|---|---|---|---|---|---|---|---|---|
| | | I | II | III | IV | V | VI | VII | VIII |
| $^1H$ (a) | $\delta CH_3P$ | 0.93 | 1.58 | 1.02 | 0.81 | 1.00 | 1.07 | 0.98 | 0.92 |
| | J(HCP) | 11.5 | 11.4 | 12.0 | 11.3 | 11.6 | 11.5 | 12.0 | 11.4 |
| | J(HCPCM) | — | 4.5 | — | — | — | — | — | 3.0 |
| | $\delta CH_2P$ | −0.70 | 0.58 | 0.84 | −0.19 | −0.02 | −0.17 | 0.22 | 0.23 |
| | J(HCP) | 11.0 | 9.8 | 9.0 | 10.5 | 9.6 | 11.3 | 12.4 | 9.0 |
| | J(HCM) | — | 35.3 | — | — | 34.9 | — | — | 127.5 |
| | $\delta CH_3M$ | — | — | 1.03 | — | — | — | −0.19 | 0.47 |
| $^{31}P$ (a) | $\delta P$ | 35.0 | 27.9 | 34.2 | 33.86 | 32.5 | 33.2 | 33.6 | 34.3 |
| | J(PCM) | — | 65.6 | — | — | 4.4 | — | — | 233.6 |
| $^{13}C$ (b) | $\delta CH_3P$ | 22.0 | — | — | — | 23.2 | — | — | — |
| | J(PC) | 66.0 | — | — | — | 57.0 | — | — | — |
| | $\delta CH_2P$ | 12.6 | — | — | — | 7.1 | — | — | — |
| | J(PC) | 34.2 | — | — | — | 37.2 | — | — | — |
| | J(CM) | — | — | — | — | 271.0 | — | — | — |

(a) All eight compounds were dissolved in benzene and tested at 35° C.; the rel. ext. TMS or $H_3PO_4$. $\delta$-data are in ppm, the J-values in hz. For the sake of simplicity the "J(HCP)-value" is here indicated as $N = [J(HCP) = J(HCPCP)]$ for the present $(A_nX)_2$-spin systems (n = 2.3). $M = ^{195}Pt, ^{113}Cd, ^{205}Tl$.

(b) {$^1H$} in benzene $d_6$ at 37° C.; $\delta$ rel. $C_6D_6$ converted to TMS.

The $\delta$ $CH_3$ and $\delta$ $CH_2$ data relate to AXX'-systems.

The J(PC) figures show the separation of the most intense outer lines.

We claim:

1. A metal-bis[nitrido-bis(dimethylphosphonium methylide)] of the formula

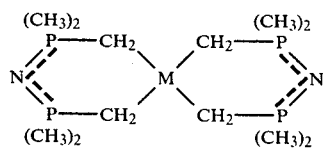

2. Lithium-[nitrido-bis-(dimethylphosphonium methylide)] of the formula

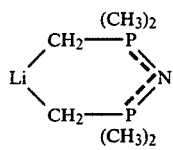

in which M stands for nickel, palladium, platinum or magnesium.

3. Dimethylgold-[nitrido-bis(dimethylphosphonium methylide)] of the formula:

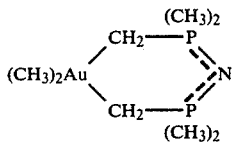

4. A process for making double ylide complexes of metals, which comprises reacting trimethyl-phosphin-imino-dimethylmethylene-phosphorane of the formula

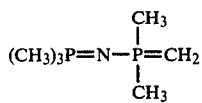

with at least one metal compound selected from [(CH$_3$)$_3$P]$_2$MX$_2$; MX$_2$; [(CH$_3$)$_3$P]$_2$Ni(CH$_3$)X; [(CH$_3$)$_3$P]$_2$Ni(CH$_3$)$_2$; [(CH$_3$)$_2$AuX]$_2$; LiR or M'R$_2$, in which M stands for nickel, palladium or platinum, X stands for chlorine, bromine or iodine, M' stands for magnesium and R stands for CH$_3$, C$_2$H$_5$, C$_3$H$_7$ or C$_4$H$_9$.

5. A process as claimed in claim 1, wherein a metal-bis[nitrido-bis(dimethylphosphonium methylide)] of the formula

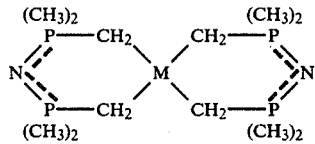

in which M stands for nickel, palladium or platinum, is made by reacting trimethylphosphin-imino-dimethyl-methylene phosphorane with bis(trimethylphosphine)-nickel, palladium or platinum dichloride in an inert organic solvent at a temperature of 10° to 110° C.

6. A process as claimed in claim 1, wherein a metal-bis[nitrido-bis(dimethylphosphonium methylide)] of the formula

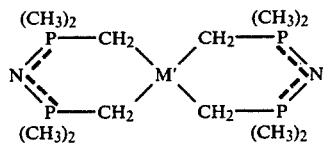

in which M' stands for magnesium, is made by reacting trimethylphosphin-imino-dimethyl-methylene phosphorane with MgR$_2$, in which R stands for CH$_3$ or C$_2$H$_5$, the reaction being effected in an inert organic solvent at a temperature of 10° to 110° C. and with agitation until evolution of gas has died down.

7. A process as claimed in claim 1, wherein the dimethylgold-[nitrido-bis(dimethylphosphonium methylide)] of the formula

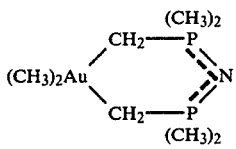

is made by reacting trimethylphosphin-imino-dimethylmethylene phosphorane with bis[dimethylgold(III)-chloride] in an inert organic solvent at a temperature of 10° to 110° C.

8. A process as claimed in claim 1, wherein the lithium[nitrido-bis(dimethylphosphonium methylide)] of the formula

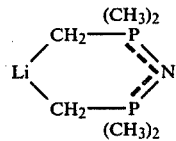

is made by reacting trimethylphosphin-imino-dimethylmethylene phosphorane with n-butyllithium in an inert organic solvent at a temperature of 0° to 110° C. until evolution of gas has died down.

* * * * *